(12) United States Patent
Stecco et al.

(10) Patent No.: US 8,920,320 B2
(45) Date of Patent: Dec. 30, 2014

(54) METHODS AND APPARATUS FOR COUPLING A HIFU TRANSDUCER TO A SKIN SURFACE

(75) Inventors: Kathryn Ann Stecco, San Jose, CA (US); Gregory Paul Darlington, Snohomish, WA (US); Jody Lloyd Johnson, Kirkland, WA (US); Howard Holman, Snohomish, WA (US); Jens U. Quistgaard, Seattle, WA (US)

(73) Assignee: Liposonix, Inc., Bothell, WA (US)

( * ) Notice: Subject to any disclaimer, the term of this patent is extended or adjusted under 35 U.S.C. 154(b) by 1960 days.

(21) Appl. No.: 11/373,419

(22) Filed: Mar. 10, 2006

(65) Prior Publication Data

US 2007/0238994 A1    Oct. 11, 2007

(51) Int. Cl.
*A61B 8/00*    (2006.01)
*A61N 7/02*    (2006.01)
*A61B 17/225*    (2006.01)
*A61N 7/00*    (2006.01)

(52) U.S. Cl.
CPC ................ *A61N 7/02* (2013.01); *A61B 8/4281* (2013.01); *A61B 2017/2253* (2013.01); *A61N 2007/0008* (2013.01)

USPC .......................................... 600/437; 600/407

(58) Field of Classification Search
USPC .................................. 600/437–449; 601/2, 3
See application file for complete search history.

(56) References Cited

U.S. PATENT DOCUMENTS

| | | | | |
|---|---|---|---|---|
| 4,002,221 A | * | 1/1977 | Buchalter | 181/0.5 |
| 4,697,579 A | * | 10/1987 | Wessels et al. | 601/4 |
| 5,231,975 A | * | 8/1993 | Bommannan et al. | 601/2 |
| 6,105,408 A | * | 8/2000 | Scharlemann | 72/31.07 |
| 6,193,658 B1 | * | 2/2001 | Wendelken et al. | 600/437 |
| 6,206,843 B1 | * | 3/2001 | Iger et al. | 601/2 |
| 6,325,769 B1 | | 12/2001 | Klopotek | |
| 8,282,554 B2 | | 10/2012 | Makin et al. | |
| 2004/0071494 A1 | * | 4/2004 | Staniforth et al. | 401/262 |
| 2006/0122509 A1 | * | 6/2006 | Desilets | 600/439 |

* cited by examiner

*Primary Examiner* — Tse Chen
*Assistant Examiner* — Vani Gupta
(74) *Attorney, Agent, or Firm* — Wood, Herron & Evans LLP

(57) ABSTRACT

Methods and apparatus are described for coupling a high intensity focused ultrasound transducer to a skin surface using water as a coupling agent.

9 Claims, 6 Drawing Sheets

METHODS AND APPARATUS FOR COUPLING A HIFU TRANSDUCER TO A SKIN SURFACE

BACKGROUND OF THE INVENTION

1. Field of the Invention

The present invention relates to methods for coupling ultrasound transducers to human skin.

2. Description of the Background Art

Ultrasound is widely used both as a diagnostic tool and a therapeutic energy source. Effective coupling of an ultrasound transducer to a patient is necessary to ensure the ultrasound energy emitted by the transducer, can traverse the boundary between the transducer and the patient, without getting reflected or scattered by the boundary between the two. The presence of air between a transducer and a patient is a major problem.

Attenuation occurs when energy is lost from the ultrasound waves as they pass through a medium. The lost ultrasound energy is absorbed by the medium and generally converted into heat. Heat buildup can quickly reach dangerous levels and cause burns on a skin surface if the heat build up occurs in the coupling medium. In addition, the amount of energy transmitted into the targeted tissue is similarly reduced.

Reflection occurs when energy is deflected by a barrier. The energy that is neither absorbed nor transmitted through the barrier is deflected back toward the energy source. In ultrasound the reflection of ultrasound energy can create a secondary focal region close to the transducer face. This may result in direct or indirect damage to the transducer. Both attenuation and reflection are negative effects that are desirably avoided.

To reduce or prevent the attenuation or reflection of ultrasound energy emitted by a transducer, a "coupling medium" is usually employed between the transducer and the skin. Existing coupling agents include a variety of aqueous solutions and mineral oils. Low power ultrasound instruments, such as diagnostic imaging transducer, may safely use more viscous solutions like hydro-gels to couple the ultrasound transducer to a patient without having to compensate for issues of attenuation or reflection. As the power of a transducer increases, there is less flexibility in acceptable coupling agents. In some HIFU procedures using lower intensity treatment regimens, mineral oil and very light hydro-gels are sufficient. However when the intensity of the treatment regimen gets very high, neither mineral oils nor hydro-gels are sufficient.

In some applications, water is used as a coupling agent. To use water with HIFU, patients are usually partially or wholly submerged in water tanks. Water is well known to have the most desirable properties for use as an acoustic transmission medium. Water is used in large tanks for testing, development and experimentation using ultrasound transducers. In actual therapy procedures, large volumes of water are needed to ensure proper coverage and coupling of the patient and to protect against adverse effects such as skin burns from attenuation of the coupling medium. In these applications, the water used in the water tanks is generally circulated through a pump and connected to a filtration system and a degassing system.

Thus there remains a need for a coupling agent that can be used with HIFU systems using high energy levels beyond those in which hydro-gels or mineral oils are suitable for coupling.

There is also a need for a method of using water as a coupling agent without requiring the bulk of filtration and degassing systems.

BRIEF SUMMARY OF THE INVENTION

One objective is to provide a coupling agent having the desired properties on minimizing attenuation and reflection with high energy HIFU applications.

Another objective is to provide a method of using the best known coupling agent in high energy HIFU applications in a quick, easy and efficient manner, negating the need for large apparatuses.

These and other objectives are met by using the disclosed methods for coupling a therapy ultrasound transducer, such as a high intensity focused ultrasound transducer, to a patient. In particular, we describe a method for coupling a high intensity focused ultrasound transducer to a skin surface. The method comprises the steps of; applying a volume of water on the skin surface so the skin surface is at least lightly moistened, placing a high intensity focused ultrasound transducer on to the moistened skin surface; and applying pressure through the ultrasound transducer so that the volume of water is distributed between the skin surface and the transducer. To lightly moisten the skin, the water will usually be applied in an amount equal to at least 0.01 ml/cm$^2$ of skin being treated, although much larger volumes can be applied. When larger volumes are applied, pressure from the transducer head will push away excess water so that a desired thickness of water remains, typically being about 0.1 mm to 1. mm (0.01 cm-0.10 cm).

In another embodiment there is a method of coupling an ultrasound transducer to a skin surface, the method comprising the steps of placing an ultrasound transducer in close proximity to a skin surface and applying a volume of water to the skin surface in a manner that the volume of water is spread out between the ultrasound transducer and the skin surface by capillary action.

In either method an addition step may involve cleaning the skin surface prior to either spraying a volume of water in the first method, or placing the ultrasound transducer in the second method. Optionally, the water may contain an anti-microbial material such as an anti-biotic, and antiseptic, and anti-fungal agent, or the like. The water may also include surfactants, surface tension modifying agents, and/or other materials which promote spreading of the water and improved contact between the transducer and skin.

DETAILED DESCRIPTION OF THE INVENTION

Figure 1:
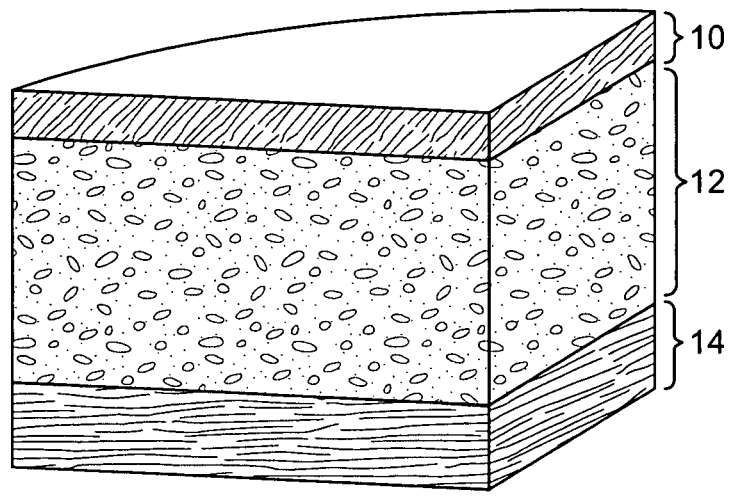
FIG. 1 illustrates a schematic cross section of normal tissue layers.

In one embodiment, there is a method for coupling a high intensity focused ultrasound transducer to a skin surface comprising the step of applying water on a skin surface to moisten the skin in a substantially even manner, The ultrasound transducer is then placed on the skin and pressed into the skin surface slightly to provide contact across the transducer face with the skin surface.

Water may be applied by spraying water on to the skin, squirting from a water bottle or any other means in which water may be delivered to a skin surface. In one example, as water is sprayed on the skin surface, droplets form or are deposited on the skin. Desirably the droplets remain small and separate from one another so the droplets do not pool together and roll off the skin surface. When the transducer is placed on the moistened skin surface, the droplets are compressed. The droplets collapse and run together to form a thin film of water. The thin film of water is held in place between the transducer and the skin by capillary attraction.

Similarly if the transducer is held in close proximity to a skin surface and water is introduced into the space between the transducer and the skin surface, the water may spread out evenly by capillary action. Even distribution may be promoted by gently rocking the transducer over the skin surface to help push out large air pockets.

The thin film of water between the transducer and skin surface need not be degassed or filtered for particles (although doing so will not adversely affect the coupling). So long as the space between the transducer and skin remains small enough for the water to be a very thin film, ordinary contaminants such as those found in tap water or drinking water do not affect transducer coupling.

Distribution of the water in the initial spraying likewise is somewhat important. Desirably the water is sprayed as a mist (from an ordinary spray bottle) and is deposited on the skin surface as droplets. Surface tension of the many droplets is sufficient to help keep the water on the skin surface regardless of the angle of the skin surface. For example the skin surface may be vertical, angled or horizontal (either right-side-up, or up-side-down) and so long as the water is not deposited on the skin in too dense a spray, the separate droplets will not pool up and roll off or drip off the skin surface. Desirably even if some water does roll off or drip off, there is sufficient water still on the skin surface to provide proper coupling. Usually, water will be applied in an amount of at least 0.01 ml/cm$^2$, usually being in the range from 0.01 ml/cm$^2$ of skin area to 0.1 ml/cm$^2$ of skin area.

Adhesion to the skin surface may be improved by adding a surfactant to the water for the initial spraying. A surfactant can lower the surface tension forces of water and allow water to spread more evenly over the skin surface. It allows for some amount of sheeting in the water's coverage area so a slightly larger volume of water can be used on a non-horizontal surface and still prevent the water from rolling off or dripping off the skin surface.

Biological agents may be added to the water. Such agents include anti-bacterial compounds, anti-fungal compounds, or general disinfectants (like alcohol). The concentration of the biological compounds or general disinfectants is desirably high enough to have the desired biological effect while low enough to not adversely affect the coupling of the transducer to the patient skin. In other embodiments, the water may be essentially pure, e.g., degassed, deionized, and passed through an 0.1 micron filter water.

As used herein, the transducer refers to the device or apparatus which either emits HIFU energy, or houses a transducer that emits HIFU energy. Due to the delicate nature of ultrasound transducers, the transducer itself may have layers of material between the actual transducer and what is commonly referred to as the transducer surface. These materials may form a lens or protective barrier for the transducer. In other embodiments, the transducer may be contained within a device having a transducer window through which ultrasound energy is designed to pass from the transducer and into the patient.

In another embodiment, there is an additional step of cleaning the skin surface prior to spraying. To reduce the incidence of adverse reactions during a HIFU procedure, it may be desirable to clean the skin surface by removing dirt, excess hair or other debris before spraying the skin surface with water. Individuals having clean or clear skin may not need any pre-cleaning before water is sprayed on their skin.

Turning now to the drawings, FIG. 1 provides a cross section illustration of normal skin, fat tissue, and a muscle layer in a patient. The upper layer is the skin layer 10, and that surface which is exposed to the outside environment. The middle layer represents fat or adipose tissue 12 which is located between the skin layer and a lower muscle lining 14. The illustrations presented are a simplification of the layers and tissue masses found in living organisms, and are provided merely for illustrative purposes. The drawing images are not provided to scale, either internally or with respect to each other.

Figure 2A:
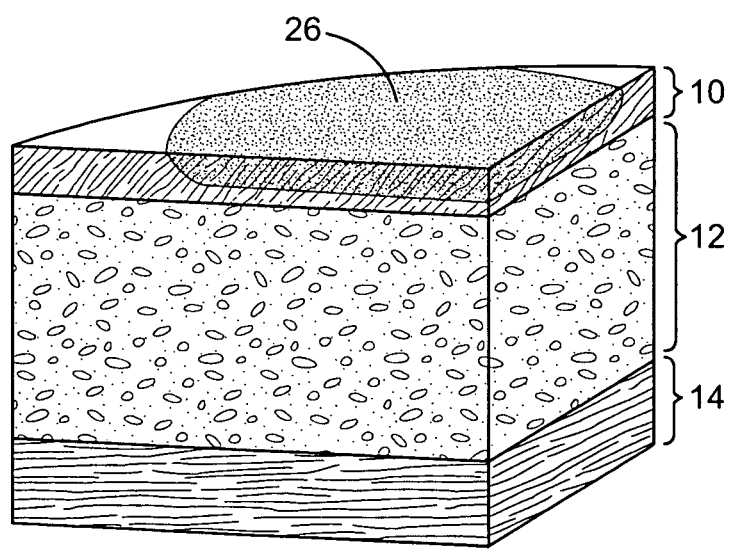
FIG. 2A illustrates a schematic cross section result using mineral oil.

FIG. 2A provides an illustration of a skin layer 10 that has been exposed to a high energy HIFU ultrasound device using mineral oil or gel as a coupling fluid. The illustration provides a contrast between the normal skin layer showing in FIG. 1, by indicating an area where the skin layer has been burned 26. This burning of the skin results from the attenuation of the ultrasound energy in the coupling layer. The skin burning is an adverse effect, and lowers the amount of ultrasound energy from penetrating into the deeper layer of tissue.

Figure 2B:
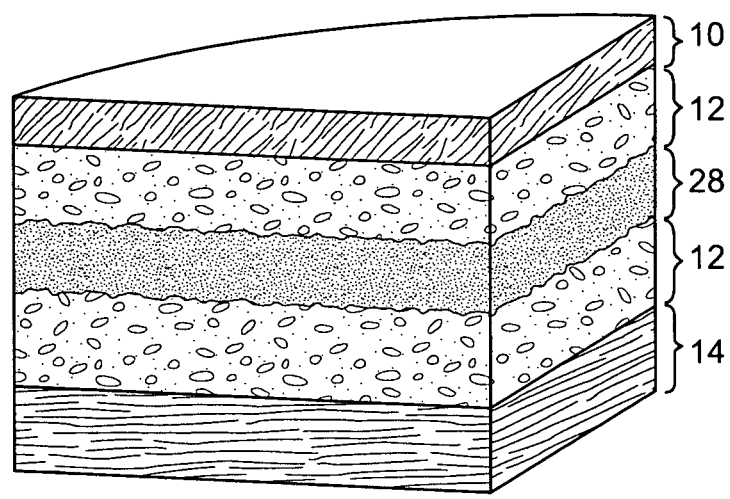
FIG. 2B-C illustrates two schematic cross section results using water.

FIG. 2B illustrates another volume of tissue after the high energy HIFU transducer has been coupled to the skin using water. The skin is unaffected and remains normal, while the sub-dermal tissue has the desired clinical effect resulting from the ultrasound treatment. A layer of destroyed adipose tissue 28 in the adipose layer 12 is the desired result from a high energy HIFU device designed specifically for the destruction of adipose tissue.

Figure 2C:
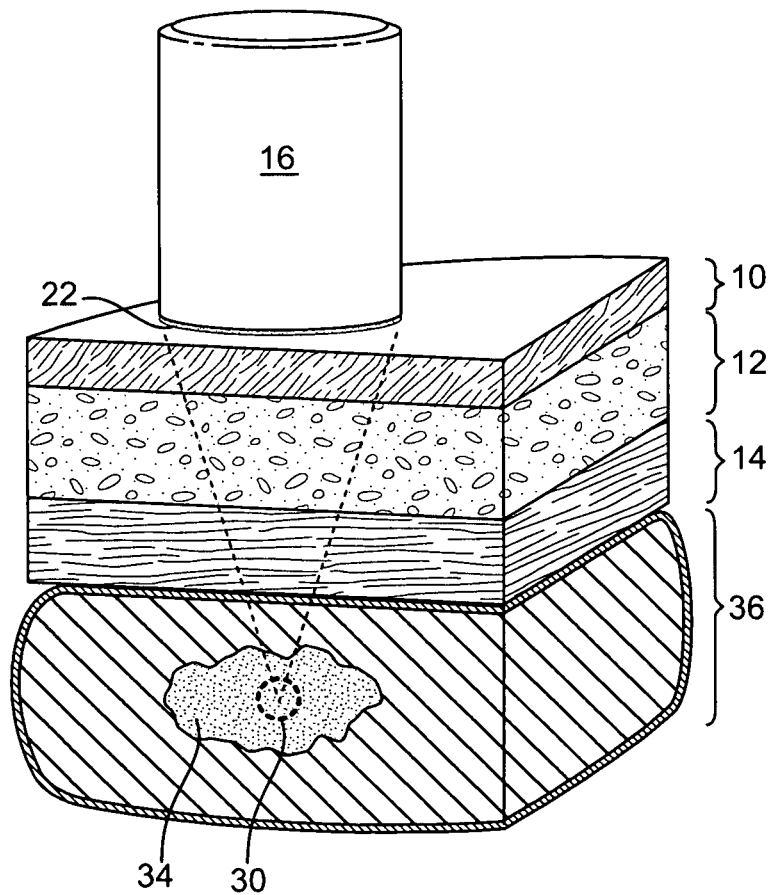

In FIG. 2C, there is another cross-sectional view of the tissue starting with the skin layer 10. Here the focal point of the transducer 16 is a diseased tissue mass 34 below the skin layer 10. The diseased tissue mass may be below the muscle layer 14 as shown; however the depth of the diseased mass 34 from the skin layer 10 is not critical. The target treatment volume 30 is located within the diseased tissue mass 34.

Before the high energy HIFU transducer is coupled to the skin surface, it may be necessary to clean the skin surface. In some patients, a cleaning step is needed while in other patients, this step is unnecessary. The cleaning step is primarily used to remove large particulate matter from the skin surface. This step may involve a simple wipe down of the skin surface area with a damp cloth, or it may involve a more detailed procedure including shaving of excessive body hair, or thorough scrubbing of the skin in the case where there may be lose skin exfoliates or other dermal issues that may affect ultrasound performance.

Figure 3A:
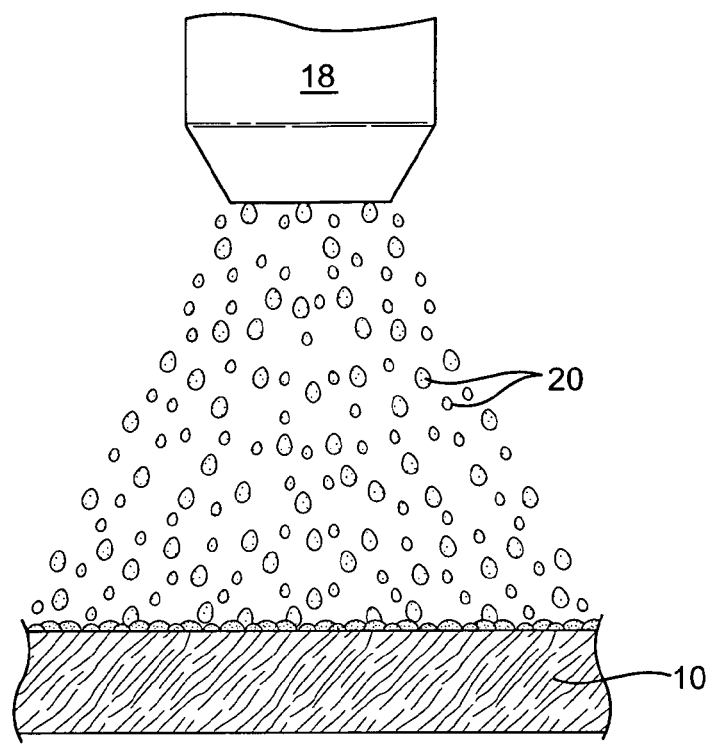
FIG. 3A-D illustrates a first method of using water as a coupling agent.

Once the skin surface is ready, either from the cleaning step, or due to the patient's innate cleanliness, water is applied to the skin surface through an applicator 18. In one embodiment, the applicator is an atomizer, and water is sprayed on to the skin surface (FIG. 3A). Water may be sprayed using any device capable of producing a spray of small water droplets, similar to a mist. Spray bottles, atomizers and similar devices are all suitable applicators for use in this embodiment. The volume of water needed to cover the skin surface varies with the size of the skin surface to be treated. Thus if the skin surface to be treated is relatively small, the volume of water needed is correspondingly small. If the skin surface area is large, the volume of water needed is proportionally larger. The water is desirably sprayed on to the skin surface so that the skin surface is moistened. Desirably the water is evenly distributed about the skin surface 10, though generally there are areas of higher concentrations of water, and lower concentrations of water. Once water is applied to the skin surface, the transducer may be used to help distribute the water by moving the transducer around or gently rocking the transducer in some fashion to help distribute the water. Even distribution of the water about the skin surface, though desirable, is not required so long as there is sufficient water to couple the transducer to the skin surface.

Figure 3B:
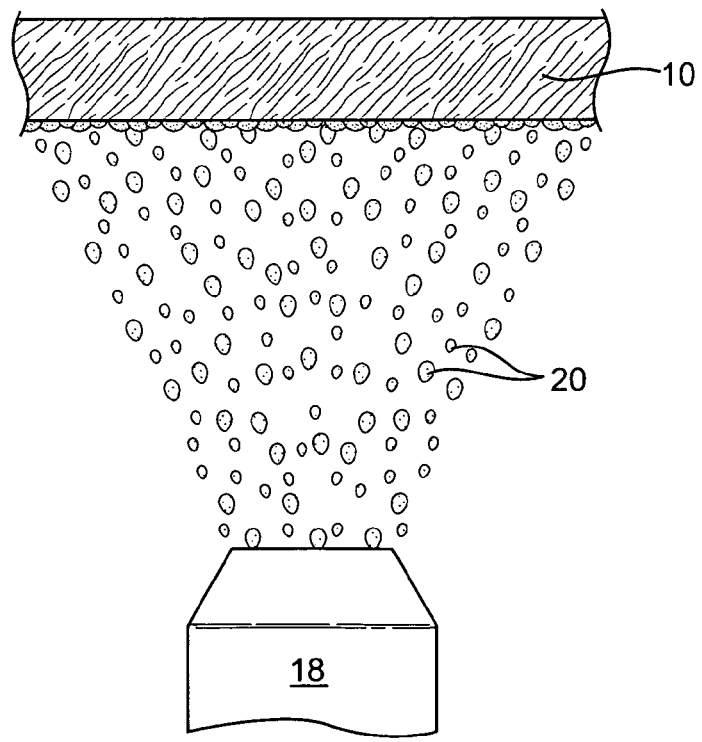

In this step it is desirable not to over-spray the skin surface. A small volume of water can be sufficient for a given skin surface. Desirably the water spray is distributed in droplets 20 that reside individually on the skin. These droplets 20 desirably remain independent of each other and do not pool together and roll or drip off the skin surface. By using water droplets 20 evenly distributed, the spraying step provides the distribution of the coupling agent that is needed. Thus the distribution of the coupling agent allows for the skin surface to be virtually any angle (showing normal in FIG. 3A, all the way to inverted in FIG. 3B).

Figure 3C:
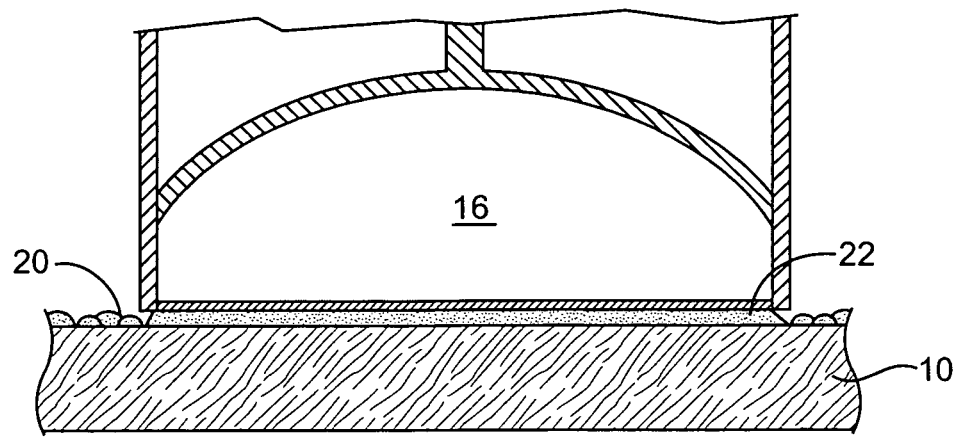
Figure 3D:
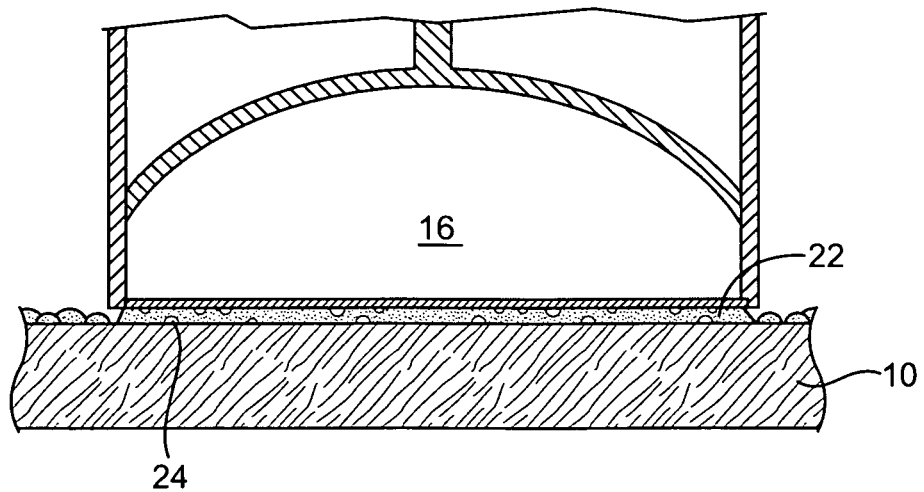
Figure 4A:
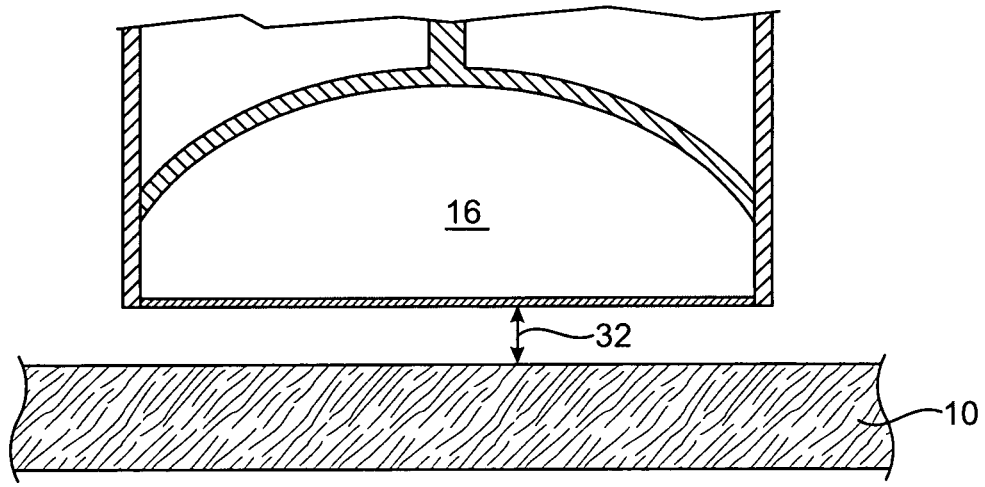
FIG. 4A-D illustrates a second method using water as a coupling agent.
Figure 4B:
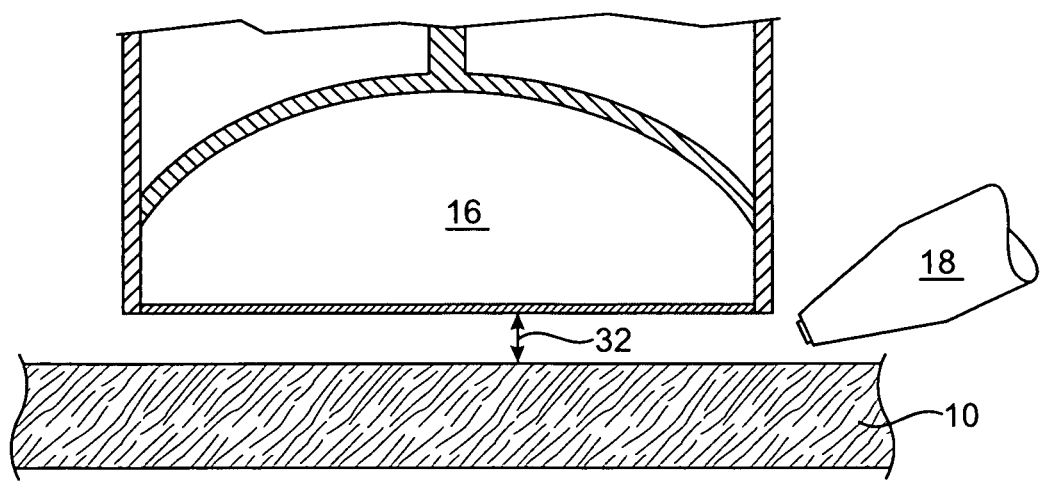
Figure 4C:
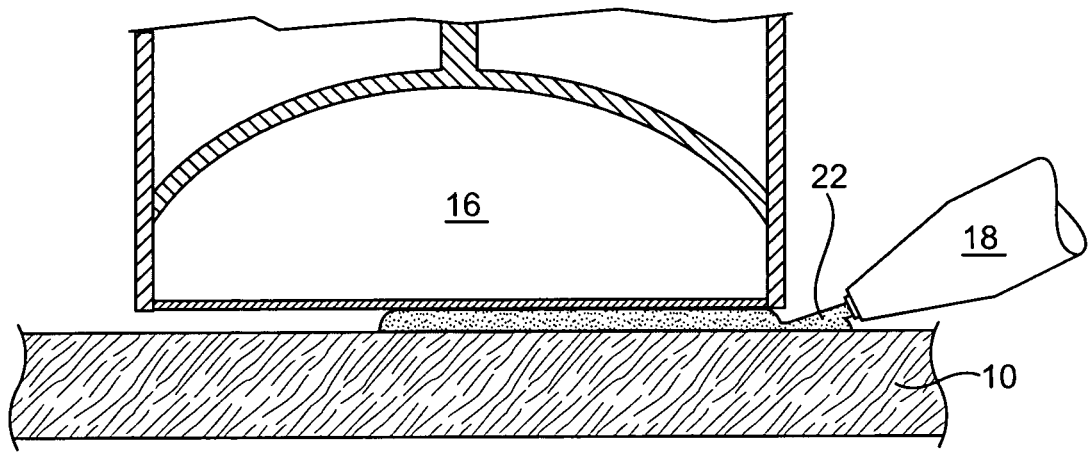
Figure 4D:
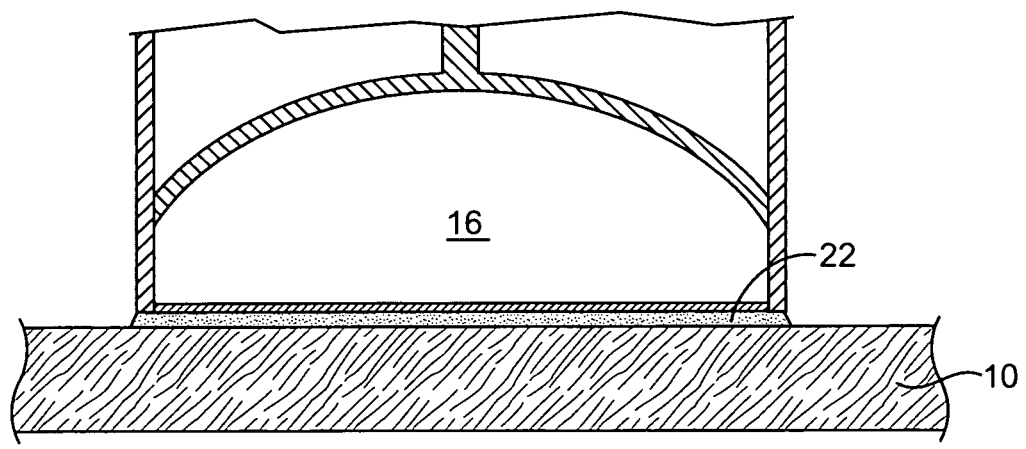

Placing the high energy HIFU transducer on the skin surface is shown in FIG. 3C. The HIFU transducer is placed over the moistened skin and set to rest on the skin surface. The water droplets are squished between the transducer face and the skin surface forming a water layer 22 (FIG. 3D). Desirably the water droplets now run together to form a thin, contiguous layer of water that serves as a coupling agent. Once water is placed on the skin surface in the manner described herein, there is generally a significant quantity of dissolved gasses in the coupling fluid. This does not appear to effect coupling.

Now the user can apply pressure through the transducer to gently push the transducer surface onto the skin surface. Excess water may be forced out from between the contact area between the skin surface and the transducer face. Desirably there is minimal or no run off, however the volume of run off after applying pressure does not affect the coupling of the transducer to the skin surface. Once the coupling steps are completed, the therapy procedure may proceed.

The method of coupling the transducer to the skin surface using water may be repeated each time the transducer is to be moved or repositioned over a new skin surface. In some instances the spraying step may cover a larger area of the skin surface than that area which the transducer face will cover. It may not be necessary to re-apply water to the skin surface if it is still sufficiently moist that the transducer can still be properly coupled to the skin surface. In this case, the transducer may be repositioned without the need to re-apply water to the skin surface.

In alternative embodiment, water may be applied to the skin surface in a wide variety of means. Successful moistening of the skin can occur by brushing or wiping water onto the skin surface, pouring or dribbling water on to the skin and then smearing the water out into an even or semi uniform layer by hand or other convenient spreading tool (e.g. spatula, brush, cloth sponge, etc.). Desirably, water is applied in an even distribution through a single step, where the volume of water is sufficient to moisten the skin without creating a large amount of run off. However the applying step may be broken down into sub-steps where the water is first applied to the skin, and then distributed over the surface area to be coupled with the HIFU transducer.

In another embodiment (FIGS. 4A-4D), the transducer can be coupled to the skin surface by first placing the transducer 16 in close proximity to the skin surface 10, and then applying a volume of water to the skin surface in manner that the volume of water is spread out between the ultrasound transducer and the skin by capillary action.

In this embodiment, the transducer is desirable placed in close proximity to the skin while allowing a small gap space between the transducer surface and the skin surface. As the water is applied to the gap space 32, it is drawn between the two surfaces and spreads out between the two surfaces. The user may "roll" the transducer face in a motion to gently rock the transducer either in a side to side fashion or a circular fashion so that water will be more evenly dispersed between the two surfaces. Desirably, air bubbles will be pushed out from between the two surfaces by these motions.

The water may be applied by using an applicator such as a syringe, spray bottle, pipette or other means that allows for the directed delivery of the water onto the skin surface, and sufficiently near the transducer so the water will get drawn between the two surfaces. Alternatively, the water may be applied directly to the transducer face first, and then the transducer may be set onto the skin surface.

In another embodiment, there is an ultrasound transducer contained within a therapy head. The therapy head has a chamber containing water, and a high intensity focused ultrasound transducer is positioned within the chamber. A sensor or trigger is used in connection with the therapy head to determine when the therapy head is in close proximity to a skin surface. The trigger or sensor can then cause the application of water to the skin surface as the therapy head is brought closer to the skin, and then into contact with the skin surface. The trigger may provide for the application of water by misting the skin surface, or secreting it through the therapy head so the water spreads across the surface of the skin or the therapy head.

The trigger may be a contact switch being positioned so that the therapy head may be placed in contact with the skin surface without the contact switch disrupting the skin line of the patient, or the trigger may be an electromagnetic sensor such as a laser or a resistance or conductive metering device. Water is diverted from the water chamber to the exterior of the therapy head using a small hose or other conduit between the water chamber and the exterior of the therapy head.

What is claimed is:

1. A method for delivering high intensity focused ultrasound energy to a skin surface, the method comprising:
   applying a thin film of fluid consisting of water having less than 1% impurities by weight on the skin surface so the skin surface is at least lightly moistened;
   placing a high intensity focused ultrasound transducer on to the moistened skin surface;
   pressing the ultrasound transducer against the skin surface so that said film of water is distributed between the skin surface and the transducer.

2. The method of claim 1, wherein the film of fluid contains a surfactant.

3. The method of claim 1, wherein the film of fluid contains an anti-microbial agent.

4. The method of claim 1, wherein the film of fluid is applied by spraying under conditions such that beading up and rolling of the water is inhibited.

5. The method of claim 1, further comprising cleaning the skin surface prior to applying the film of fluid on the skin surface.

6. The method of claim 1, further comprising repositioning the high intensity focused ultrasound transducer on the skin surface.

7. The method of claim 1, wherein applying the film of fluid comprises spraying the volume of fluid.

8. The method of claim 1, wherein applying comprises:
applying the film of fluid on to a small skin surface; and
spreading the film of fluid over a larger skin surface.

9. The method of claim 1, wherein the film of fluid is applied at least 0.01 ml/cm2 of skin surface.

* * * * *